US00RE36104E

United States Patent [19]

Solar

[11] E Patent Number: Re. 36,104

[45] Reissued Date of Patent: Feb. 16, 1999

[54] DILATION CATHETER WITH ECCENTRIC BALLOON

[75] Inventor: Ronald J. Solar, San Diego, Calif.

[73] Assignee: Cordis Corporation, Miami Lakes, Fla.

[21] Appl. No.: 853,209

[22] Filed: May 9, 1997

Related U.S. Patent Documents

Reissue of:

[64] Patent No.: 5,413,557
Issued: May 9, 1995
Appl. No.: 111,304
Filed: Aug. 24, 1993

U.S. Applications:

[63] Continuation of Ser. No. 969,946, Oct. 30, 1992, Pat. No. 5,315,747.

[51] Int. Cl.[6] ..... A61M 29/00

[52] U.S. Cl. ..... 604/96; 606/194

[58] Field of Search ..... 604/96, 97–104, 604/280, 283; 606/191–194

[56] References Cited

U.S. PATENT DOCUMENTS

| | | | |
|---|---|---|---|
| 3,811,448 | 5/1974 | Morton | 604/102 |
| 4,195,637 | 4/1980 | Gruntzig et al. . | |
| 4,323,071 | 4/1982 | Simpson et al. . | |
| 4,493,711 | 1/1985 | Chin et al. . | |
| 4,573,470 | 3/1986 | Frisbee et al. . | |
| 4,619,262 | 10/1986 | Frisbee et al. . | |
| 4,641,649 | 2/1987 | Walinsky . | |
| 4,643,186 | 2/1987 | Walinsky . | |
| 4,762,129 | 8/1988 | Bonzel . | |
| 4,790,315 | 12/1988 | Mueller et al. . | |
| 5,040,548 | 8/1991 | Yock . | |
| 5,045,061 | 9/1991 | Seifert et al. | 604/96 |
| 5,061,273 | 10/1991 | Yock . | |
| 5,090,958 | 2/1992 | Sahota | 604/96 |

*Primary Examiner*—John D. Yasko
*Attorney, Agent, or Firm*—Michael W. Montgomery

[57] ABSTRACT

This invention relates to a balloon dilatation catheter. The balloon dilatation catheter comprises a first, inflation lumen extending therethrough and having distal and proximal ends, the distal end of the first lumen opening into and being in fluid communication with the interior of an inflatable dilatation balloon having distal and proximal ends, and a second lumen extending coextensively with and exterior to the dilatation balloon.

44 Claims, 7 Drawing Sheets

DILATION CATHETER WITH ECCENTRIC BALLOON

Matter enclosed in heavy brackets [ ] appears in the original patent but forms no part of this reissue specification; matter printed in italics indicates the additions made by reissue.

*This application is a reissue of Ser. No. 08/111,304, filed Aug. 24, 1993, now U.S. Pat. No. 5,413,557, which is a continuation-in-part of Ser. No. 969,946, filed Oct. 30, 1992, now U.S. Pat. No. 5,315,747.*

FIELD OF THE INVENTION

This invention is directed to a catheter that utilizes a balloon to dilate structures or stenoses within the human body. More particularly, this invention is directed to a dilatation catheter having an eccentrically positioned balloon.

BACKGROUND OF THE INVENTION

The use of balloon catheters to treat strictures, stenoses, or narrowings within various parts of the human body is well known and is the subject of many patents. For example, Gr üntzig, U.S. Pat. No. 4,195,637, Simpson and Robert, U.S. Pat. No. 4,323,071, Bonzel, U.S. Pat. No. 4,762,129, Yock, U.S. Pat. Nos. 5,040,543 and 5,061,273, Samson et al., U.S. Pat. No. 4,573,470, Chin et al., U.S. Pat. No. 4,493,711, Mueller et al., U.S. Pat. No. 4,790,315, Walinsky et al., U.S. Pat. No. 4,641,649Rosen et al., U.S. Pat. No. 4,643,186, and others, teach that balloon catheters can be used to dilate stenoses in blood vessels. In each design, the balloon has a generally cylindrical shape, positioned in a concentric manner in relation to the catheter shaft, and bonded distally and/or proximally to the shaft. When an operator attempts to pass a dilatation balloon pass a dilatation balloon having such a design through a very tight opening in a stenosis, the balloon may bunch up, i.e., fold up longitudinally like an accordion, as shown in FIG. 1, and the catheter will not pass through the stenosis. A balloon catheter in which the balloon is bonded to the shaft for its entire length would eliminate this problem.

Inflation of a concentrically mounted balloon results in a uniform force circumferentially applied to the stenotic lesion. However, the structure or morphology of the lesion is rarely uniform, and harder portions will require more force to dilate than will softer areas. This has necessitated the practice of inflating the balloon at very high pressures, causing overdistention, dissection, and tearing. In addition, at high pressures, a dilatation balloon may rupture, resulting in serious complications. Thus, there is a need for a balloon catheter which can apply a focused, variable force for dilatation, at lower pressures.

In prior art dilatation balloon catheters, the shaft segment within the balloon may be a solid wire (Frisbee and Samson), or it may be a hollow and open-ended tube which allows the catheter to be moved over a guidewire (Simpson/Robert, Bonzel, Yock). The catheter of Mueller et al., a representative structure of which is shown in FIG. 2, has small holes in the shaft proximal to the balloon to allow blood to enter, for the intended purpose of allowing blood to perfuse the vessel while the balloon is inflated. Since the blood impacts the balloon, turns to enter the small holes in the shaft, and then turns again to exit the catheter in the proximal direction, this design promotes turbulent blood flow of the type that often results in hemolysis and thrombosis. The balloon of Walinsky is porous and is intended to deliver a therapeutic agent to the lesion while the balloon is inflated. Since the inflation pressure of the balloon is often high to effect dilatation, the drug may exit the pores in the balloon at a velocity that would injure or even perforate the vessel.

Thus, there is a need for a balloon dilatation catheter with a lumen positioned external to the balloon, such that the lumen could be used for therapeutic means (e.g., blood perfusion, drug delivery) during balloon inflation.

OBJECTS OF THE INVENTION

It is an object of the invention to provide a balloon dilatation catheter that has one or more lumens positioned exterior to the balloon.

It is also an object of the invention to provide a balloon dilatation catheter in which the balloon is eccentric to the shaft.

It is a further object of the invention to provide a balloon dilatation catheter in which the balloon is eccentric to a guidewire lumen.

It is yet a further object of the invention to provide a balloon dilatation catheter in which the dilating force applied to a stricture is focused and non-uniform around its circumference.

It is furthermore an object of the invention to provide a balloon dilatation catheter in which the balloon is attached to the shaft of the catheter for the entire length of the balloon.

DETAILED DESCRIPTION OF THE INVENTION

According to the invention herein, the balloon of a balloon dilatation catheter is mounted eccentric to the catheter shaft, and/or the distal section of the guidewire lumen. The distal section of the catheter comprises two or more substantially coextensive lumens wherein the distal portion of one lumen terminates in a dilatation balloon. Another, second lumen has proximal and distal openings to receive a guidewire in a sliding fit. The second lumen may be of substantially equivalent length to the first lumen, or, alternatively, be shorter, such that the proximal opening of the second lumen is substantially distal to the proximal opening of the first lumen.

In a preferred embodiment, the catheter comprises two substantially coextensive lumens of equal length, wherein the distal portion of one lumen terminates in a dilatation balloon, and the second lumen is open at its distal end and is interrupted near its distal end to provide an opening for a guidewire that extends distally through the open distal end. In this embodiment, the second lumen may have a pushing wire that extends from the proximal portion of the catheter to a point proximal, adjacent, or distal to the opening. Preferably the second lumen engages a radiopaque marker that functions to help break plaque as well as to provide means for locating the position of the catheter balloon within the vessel.

Figure 1:
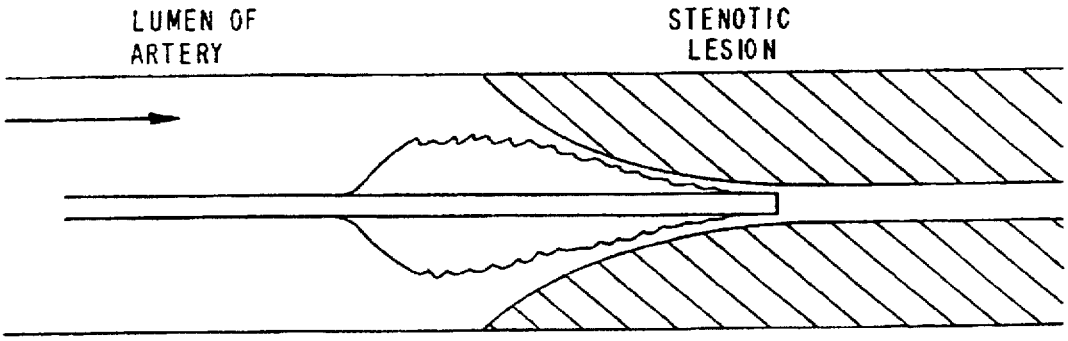
FIG. 1 PRIOR ART
FIG. 1 is a cross-sectional representation of the distal portion of a prior art balloon catheter attempting to cross a tight stenosis.
Figure 2:
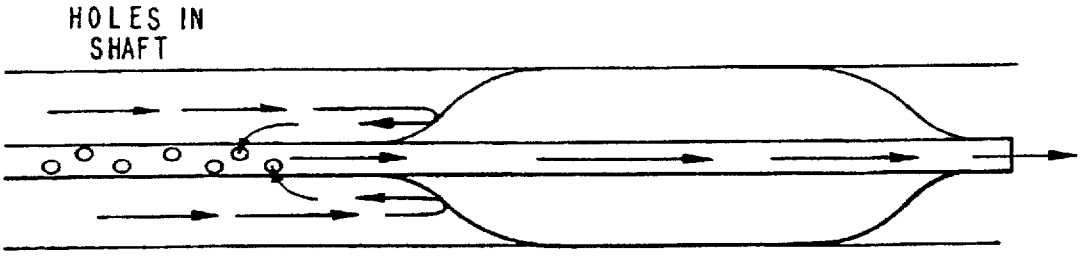
FIG. 2 PRIOR ART
FIG. 2 is a cross-sectional view of a prior art perfusion catheter.
Figure 3:
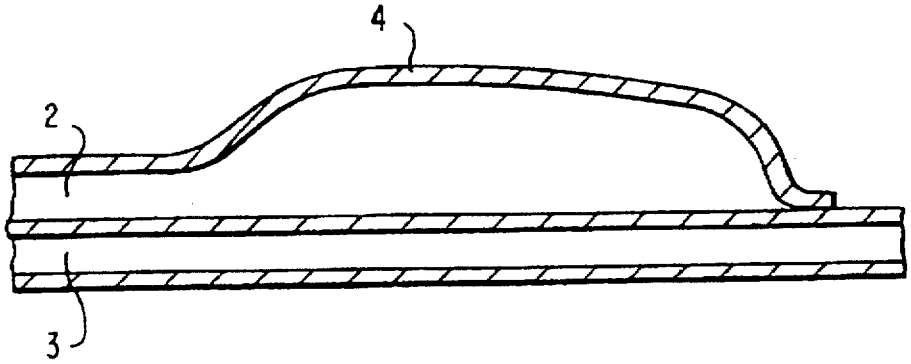
FIGS. 3 and 3a are each a cross-sectional view of the distal portion of the invention illustrating the basic structure of the design.
Figure 3A:
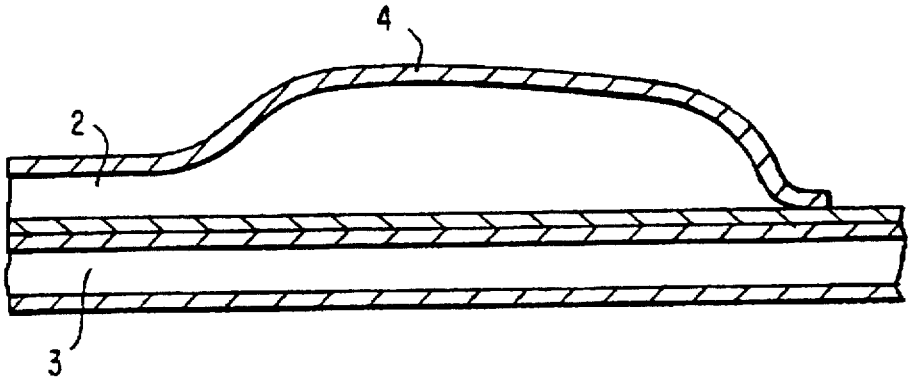

The invention can perhaps be better appreciated by making reference to the drawings. The basic structure of the design is shown in FIGS. 3 and 3a. FIGS. 3 and 3a depict the distal portion of a balloon dilatation catheter 1 having coextensively extending lumens 2 and 3. Lumen 2 terminates in a dilatation balloon 4 which is inflated and deflated through lumen 2. Lumen 3 may be bonded to balloon 4 as shown in FIG. 3a or preferably formed from one piece as shown in FIG. 3.

Figure 4:
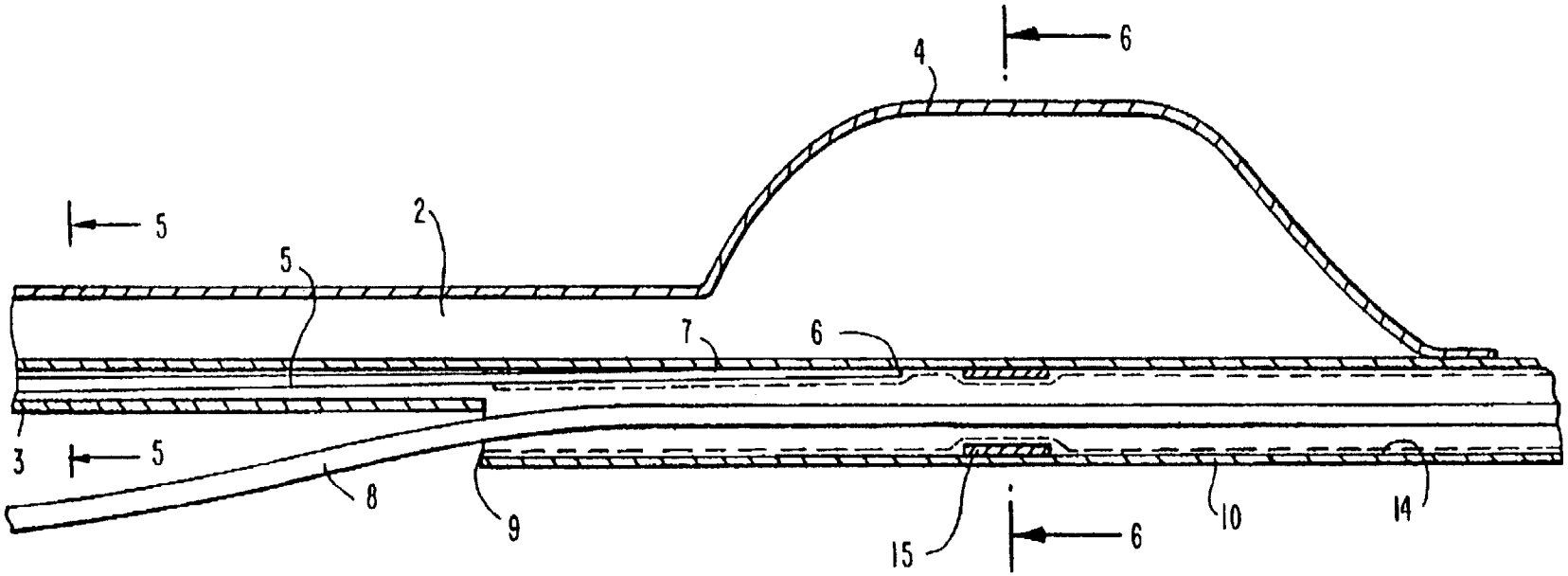
FIG. 4 is a cross-sectional view of the distal portion of an embodiment of a dilatation balloon catheter according to the invention.

In a preferred embodiment, shown in FIG. 4, lumen 3 contains pushing wire 5, which extends from the proximal end (not shown) of catheter 1 to a position 6 proximal, adjacent to, or within balloon 4. The distal portion of pushing wire 5 is secured by closure, e.g., heat-shrinking, of lumen 3, by insertion of a plug, or by other holding means. Also, the distal portion 7 of pushing wire 5 is preferably tapered distally to provide a smooth transition in axial stiffness. The pushing wire 5 will become less stiff as the diameter of pushing wire 5 narrows in the distal direction. The tapering is substantially linear over the distal portion of the pushing wire 5. Optionally, instead of linear tapering, the tapering may be stepped, in discrete reductions, or otherwise nonlinear.

The distal portion 10 of lumen 3 is enlarged, beginning at a location proximal to the balloon. Opening 9 allows a guidewire 8 to enter and extend distally through the open distal end of lumen 3. Preferably, a lubricious lining 14 and a radiopaque marker 15 are included in the enlarged section 10. Lubricious lining 14 may function to hold the distal portion of pushing wire 5 between the inner surface of lumen 3 and the outer surface of lubricious lining 14.

Figure 5:
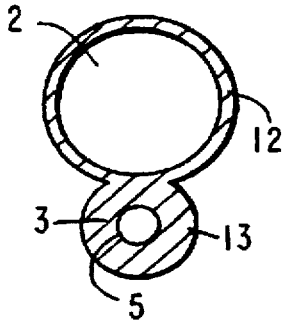
FIG. 5 is a cross-sectional view in the proximal direction of the embodiment shown in FIG. 4.

FIG. 5 represents a cross-sectional view showing how lumens 2 and 3 relate to one another and how pushing wire 5 is positioned within lumen 3. Lumen walls 12 and 13 can each have a thickness of from about 0.3 to 20 mil, preferably from about 0.5 to 10 mil.

Figure 6:
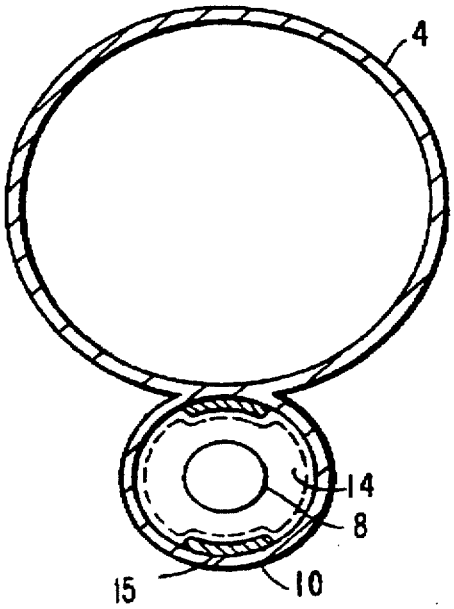
FIG. 6 is a cross-sectional view through the balloon of the embodiment shown in FIG. 4.

FIG. 6 represents a cross-sectional view through the center of the balloon of this embodiment. This figure shows how the balloon relates to the enlarged section 10 of lumen 3, and to guidewire 8. Preferably, a radiopaque marker 15 is sandwiched between the outer surface of lubricious lining 14 and the inner surface of the wall of enlarged section 10. In an additional embodiment, the catheter may have more than one external lumen, preferably two.

Although FIGS. 5 and 6 each appear to represent a one-piece construction, as shown in FIG. 3a, lumens 2 and 3 may be defined by tubes adhesively or otherwise bonded together.

Figure 7:
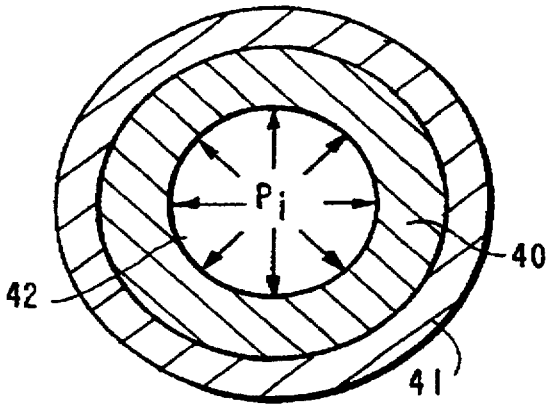
FIG. 7 PRIOR ART
FIGS. 7 and 8 are representations of cross-sections of dilatation balloon catheters according to the prior art and the invention, respectively, within a stricture to be dilated.
Figure 8:
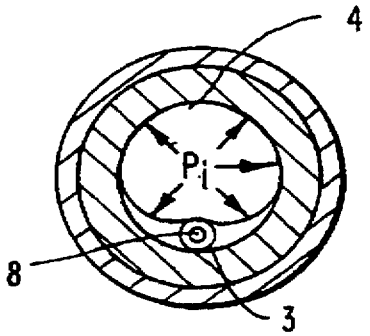

FIGS. 7 and 8 show dilatation balloon catheters, according to the prior art and the invention, respectively, in the application of dilating a stenotic lesion 40 in a blood vessel 41. As the balloon of a dilatation catheter is inflated, it exerts a force, F, that corresponds to the inflation pressure. The pressure that is exerted against the lesion is proportional to this force, F, divided by the area upon which the force is acting (the "contact area"). As shown in FIG. 7, for prior art balloon catheters the contact area is equal to the lateral surface area of the balloon 42. For the catheter of this invention (FIG. 8) the contact area is not coextensive with the lateral surface area of the balloon 4. At one point the contact area is equal to the lateral surface area of balloon 4. However, at another point, the contact area is equal to the lateral surface area of the tube that defines lumen 3. Since lumen 3 has a much smaller area of contact against the lesion than does the balloon 4, the pressure exerted at that point is much greater. Therefore, unnecessarily high balloon inflation pressures can be avoided since this design accentuates and focuses the radial force against the lesion adjacent to lumen 3.

The concepts discussed above for FIG. 8 can be represented mathematically by the formulae shown below:

$$P = \frac{F}{A} \tag{1}$$

Where P=pressure exerted against a lesion at a given point;

F=Force generated by inflating the balloon; and

A=Contact area.

At the location where the balloon 4 makes contact with the lesion 40, the pressure exerted against the lesion is given by $$P_B = \frac{F}{A_B} \tag{2}$$

where $A_B$=lateral surface area of the balloon

At the location where the outer wall of lumen 3 makes contact with the lesion 40, the pressure exerted against the lesion is $$P_{L3} = \frac{F}{A_{L3}} \tag{3}$$

where $A_{L3}$=lateral surface area of the outer wall of lumen 3.

Since the lateral surface area of the balloon is much greater than that of the outer wall of lumen 3, $$A_B = CA_{13} \tag{4}$$

where C=some factor greater than 1.

The ratio of $P_{L3}$ to $P_B$ is determined by dividing equation (3) by equation (2) and substituting equation (4)

$$\frac{P_{L3}}{P_B} = \frac{\frac{F}{A_{L3}}}{\frac{F}{CA_{L3}}} \tag{5}$$

$$P_{L3} = CP_B$$

Therefore, for a given balloon inflation pressure, the pressure exerted against the portion of the lesion adjacent lumen 3 is greater than that exerted against the portion of the lesion adjacent to the balloon.

Figure 9:
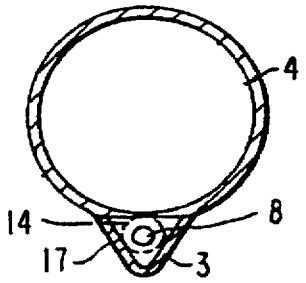
FIG. 9 is a cross-sectional view of the distal portion of another embodiment of the invention.
Figure 10:
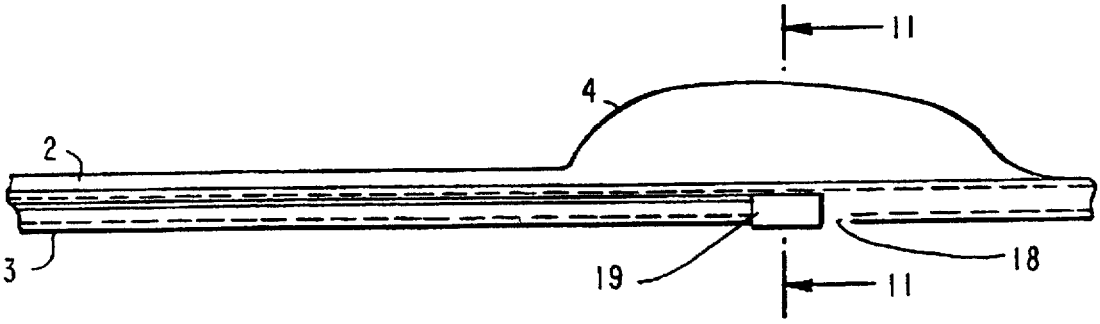
FIG. 10 is a cross-sectional view of a further embodiment of the invention.
Figure 11:
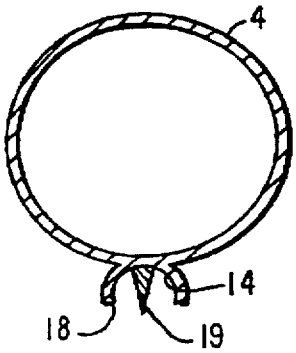
FIG. 11 is a cross-sectional view of the line 11—11 of the embodiment shown in FIG. 10.

Additional embodiments, illustrated in FIGS. 9 to 11, provide for alternate means to achieve the concentration or focusing of the dilating force. For both of these embodiments, the section in the eccentric lumen 3 that is associated with the dilatation, i.e., adjacent to the balloon, has means that form an even smaller contact area with the lesion. Such means provide somewhat of a sharp edge, similar to a knife edge, to cut the lesion as the balloon is inflated. In FIG. 9, the metal band 17 that serves as a radiopaque marker has a triangular shape, and is positioned within lumen 3 such that one side of the triangle 17 is located under the balloon, and the opposite apex of the triangle is against the lesion. In the embodiment of FIGS. 10 and 11, a section of lumen 3 under the balloon is cut away. A triangularly shaped wire or guidewire, or some other knife edge or cutting instrument 19, can be safely passed through lumen 3 and positioned directly at the lesion through the opening 18. This opening in lumen 3 will also allow drugs to be delivered directly to the lesion.

The rapid exchange embodiment of the invention, for example, the embodiment shown in FIG. 4, can also function as an improved, more efficient perfusion catheter. With the guidewire removed from lumen 3, blood will flow through lumen 3 while the balloon is inflated. Since the openings in lumen 3 are collinear with the artery, i.e., collinear with the direction of the flow of blood, and are large (compared to the side-hole openings of previously described perfusion catheters), there will be significantly less turbulence in the blood flow through lumen 3. As a result, there will be significantly greater blood flow, and reduced hemolysis compared to previously described perfusion catheters. Moreover, in an embodiment that employs more than one eccentric lumen, and/or an embodiment like that of FIG. 4 in which pushing wire 5 is replaced with a sedable guidewire, a guidewire may be left in place (i.e., in a lumen) while blood flows through an open lumen.

According to the invention, the distal section of a balloon dilatation catheter comprises at least two substantially, longitudinal coextensive lumens wherein one lumen terminates in a dilatation balloon and at least one other lumen is positioned outside, i.e., eccentric to the balloon.

The lumen walls 12 and 13 are comprised of materials conventional to balloon dilatation catheters. Suitable materials include polyolefins such as polyethylene, polyethylene terepthalate, polyurethanes, polyesters, and various copolymers thereof. When used, pushing wire 5 can be made from any rigid, medically acceptable material suitable for such use, including, but not limited to wires or hypotubes comprised of stainless steel or other rigid materials.

Figure 12:
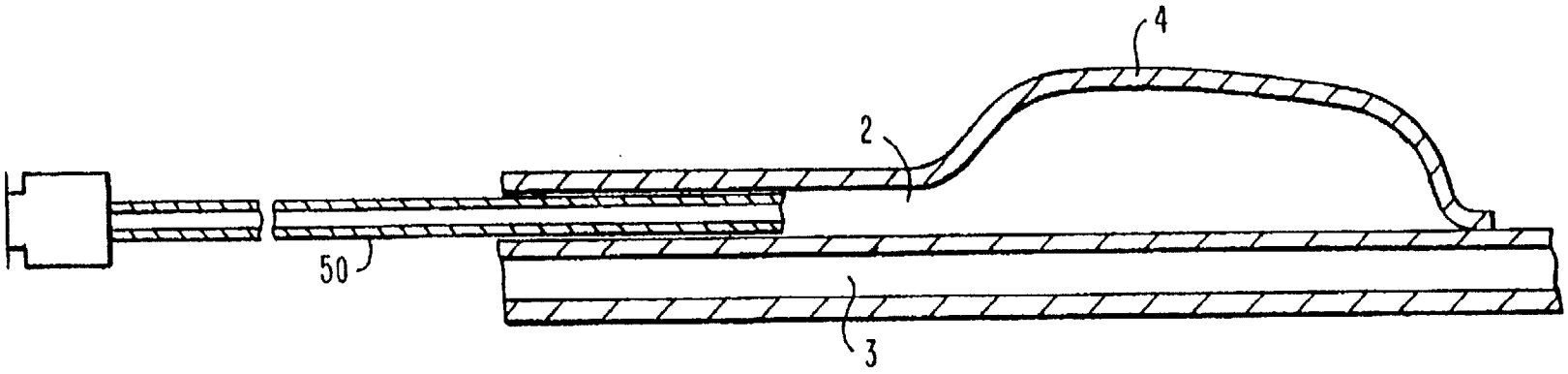
FIG. 12 is a cross-sectional view of a yet further embodiment of the invention.

The construction according to the invention leads to flexibility in product design. For example, the choice of pushing wire allows the designer to impart various features to the catheter in the form of various flexibility and pushability combinations. Also, a hollow pushing wire, or deletion or removal of the pushing wire, would facilitate infusion of fluids, drugs, and/or contrast media through the catheter into the distal vasculature. Similarly, lumen 2, used to inflate the balloon, could have a composite structure, for example, with a distal segment coextensive with lumen 3 as described above, and a proximal segment made from a hollow wire, such as a hypotube 50. An example of such an embodiment is shown in FIG. 12. Further, it is within the scope of the invention that catheter 1 may have at least one additional, coextensive lumen that would similarly facilitate infusion of liquids, drugs and/or contrast media. For example, a catheter 1 with a third, coextensive lumen open at its distal end could have several possible applications.

In a preferred embodiment of the invention, as shown in FIG. 4, a lubricious coating or a section of thin tubing 14 of lubricious material is sealed into enlarged section 10. There are several known materials suitable for this purpose, such as polytetrafluoroethylene (available as TEFLON® from dupont), polyethylenes, polysiloxanes, etc. In this embodiment the tubing section 14 can hold the distal portion 7 of pushing wire 5, as well as radiopaque marker 15 or 17, in position.

According to a another embodiment of the invention a slitting means (not shown) is mounted proximally on guidewire 8. Then, as the catheter 1 is withdrawn, the enlarged section engages the slitting means, the enlarged section 10 is slit, and catheter 1 is separated from guidewire 8. This would eliminate the requirement for the operator to change hands as catheter 1 is removed.

The catheter 1 may have visual length markings along its shaft that would enable the operator to predict when the catheter 1 would exit the guiding catheter into the vasculature. This would reduce the fluoroscope time. The preferred design would put the markings directly on the pushing wire 5 (heat shrink tubing rings, inks, paints, etc.). Since pushing wire 5 is encapsulated within the second lumen 3, the markings would not be exposed to the patient (i.e., markings would not come off, and materials which could be toxic if exposed may be used).

The preparation of a catheter 1 according to the invention can be carried out by methods and techniques known to or discernible by those skilled in the art. Furthermore, preparation of a catheter 1 is described and taught in Applicant's copending, commonly assigned, U.S. patent application Ser. No. 07/969,946, filed Oct. 30, 1992, and U.S. patent application Ser. No. 08/087,428, filed Jul. 2, 1993, both of which are incorporated herein by reference.

Guidewire 8 may be a conventional guidewire, preferably a spring guidewire, as is well known. Typical guidewires are shown in U.S. Pat. Nos. 4,757,827, 4,815,478, 4,813,434, 4,619,274, 4,554,929, 4,545,390, 4,538,622, 3,906,938, 3,973,556, and 4,719,924, all of which are incorporated herein by reference. In addition, the shaft of guidewire 8 could be solid or hollow, such as a hypotube, with an open distal end, to facilitate drug infusion.

Operation and use of the angioplasty apparatus of the invention, an embodiment of which is shown in FIG. 4, may now be briefly described as follows: A guiding catheter is inserted into the coronary artery in a conventional manner. The guidewire 8 is then introduced into the guiding catheter and advanced to and across the lesion. Now, the balloon dilatation catheter is inserted onto the guidewire and then advanced along the guidewire 8 to and across the lesion.

After the balloon 4 has crossed the stenosis or lesion, the balloon 4 can be inflated in a conventional manner by introducing a radiopaque contrast liquid through the lumen 2. After the inflation has occurred and the desired operation has been performed by enlarging the opening in the stenosis, the balloon dilatation catheter 1 can be removed very rapidly by holding the guidewire 8 stationary and withdrawing the balloon dilation catheter.

If it is ascertained by the operator that additional dilatation of the stenosis is desired and that a larger balloon should be inserted into the stenosis, this can be accomplished very rapidly by selecting the desired size of balloon dilation catheter and repeating the aforementioned procedure. The balloon of the new dilatation catheter can be inflated in the same manner as hereinbefore described. If necessary, even another exchange procedure can be readily accomplished in the same manner as hereinbefore described utilizing a still larger balloon dilatation catheter if that turns out to be necessary.

After the desired amount of dilation of the stenosis or lesion has been accomplished, the balloon dilatation catheter can be removed and thereafter the guiding catheter can be removed.

As would be appreciated by those skilled in the art, for embodiments in which lumens 2 and 3 are substantially the same lengths, operation and use of the apparatus would be in the same manner as for a conventional over-the-wire balloon dilatation catheter.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A balloon dilatation catheter which comprises:

a catheter shaft defining a first, inflation lumen and a second lumen, each of said first and second lumens having proximal and distal ends, and an inflatable dilatation balloon having proximal and distal ends, wherein the distal end of said first lumen opens into and is in fluid communication with the interior of the dilatation balloon and the second lumen extends longitudinally with the first lumen, the proximal end of the second lumen being adjacent to the proximal end of the first lumen, the distal end of the second lumen being open and distal to the distal end of the first lumen, the section of the second lumen distal to the proximal end of the dilatation balloon being exterior to the dilatation balloon, the distal end of the second lumen being open and distal to the distal end of the dilatation balloon, and the second lumen being sufficiently linear to allow the catheter to be slidingly advanced over a guidewire.

2. The catheter of claim 1, wherein the first inflation lumen is a metal hypotube.

3. The catheter of claim 1, wherein a radiopaque marker is located within the second lumen at a point between the proximal and distal ends of the balloon.

4. The catheter of claim 3, wherein the radiopaque marker has a triangular shape.

5. The catheter of claim 3, wherein the radiopaque marker has an outwardly extending sharp edge opposite the balloon.

6. A balloon dilatation catheter system which comprises one or more catheters of claim 1 and a guidewire.

7. The system of claim 6, wherein each catheter has a dilatation balloon of varying size.

8. The catheter of claim 1, wherein a portion of the distal section of the second lumen has an opening located between the proximal and distal ends of the balloon.

9. The catheter of claim 8, wherein a cutting instrument may be passed within the second lumen and positioned at the opening in the second lumen that is located between the proximal and distal ends of the balloon.

10. The catheter of claim 1, comprising one or more additional lumens.

11. The balloon dilatation catheter of claim 1, wherein the diameter of the second lumen is smaller than the diameter of the inflated dilatation balloon.

12. The balloon dilatation catheter of claim 1, wherein the balloon is bonded axially along its entire length to the second lumen.

13. The balloon dilatation catheter of claim 1, wherein the balloon and the second lumen are made from one piece.

14. The catheter of claim 1, wherein a radiopaque marker is located within the second lumen at a point between the proximal and distal ends of the balloon.

15. The catheter of claim 14, wherein the radiopaque marker has a triangular shape.

16. The catheter of claim 14, wherein the radiopaque marker has an outwardly extending sharp edge opposite the balloon.

17. A balloon dilatation catheter system which comprises one or more catheters of claim 1 and a guidewire.

18. The system of claim 17, wherein each catheter has a dilatation balloon of varying size.

19. A balloon dilatation catheter which comprises:

a catheter shaft defining a first, inflation lumen and a second lumen, each of said first and second lumens having proximal and distal ends, and an inflatable dilatation balloon having proximal and distal ends, wherein the distal end of the first lumen opens into and is in fluid communication with the interior of the dilatation balloon, the proximal end of the second lumen being open and being located substantially distal to the proximal end of the first lumen, the section of the second lumen distal to the proximal end of the dilatation balloon being exterior to the dilatation balloon, the distal end of the second lumen being open and distal to the distal end of the dilatation balloon, and the second lumen being sufficiently linear to allow the catheter to be slidingly advanced over a guidewire.

20. The catheter of claim 19, wherein the diameter of the second lumen is smaller than the diameter of the inflated dilatation balloon.

21. The catheter of claim 19, wherein the balloon is bonded axially along its entire length to the second lumen.

22. The catheter of claim 19, wherein the balloon and the second lumen are made from one piece.

23. The catheter of claim 19, wherein the first inflation lumen is a metal hypotube.

24. The catheter of claim 19, wherein a radiopaque marker is located within the second lumen at a point between the proximal and distal ends of the balloon.

25. The catheter of claim 24, wherein the radiopaque marker has a triangular shape.

26. The catheter of claim 24, wherein the radiopaque marker has an outwardly extending sharp edge opposite the balloon.

27. A balloon dilatation catheter system which comprises one or more catheters of claim 19 and a guidewire.

28. The system of claim 27, wherein each catheter has a dilatation balloon of varying size.

29. A balloon dilatation catheter which comprises a first, inflation lumen extending therethrough and having distal and proximal ends, the distal end of said first lumen opening into and being in fluid communication with the interior of an inflatable dilatation balloon having distal and proximal ends, and a second lumen extending coextensively with the first lumen, having proximal and distal ends, wherein the proximal end of the second lumen is adjacent to the proximal end of the first lumen, the distal end of the second lumen is open and distal to the distal end of the balloon, and wherein the distal section of the second lumen is exterior to the balloon and has an opening proximal, adjacent, or distal to the proximal end of the dilatation balloon, and the section of the second lumen distal to the opening is enlarged as compared to the proximal section of the second lumen.

30. The catheter of claim 29, wherein the proximal, unenlarged section of the second lumen contains a pushing wire.

31. The catheter of claim 30, wherein the pushing wire has proximal and distal ends and said distal end is positioned at or near the opening of the second lumen.

32. The catheter of claim 29, wherein the enlarged portion of the second lumen comprises lubricious material.

33. The catheter of claim 32, wherein the lubricious material is in the form of tubing within the enlarged section.

34. The catheter of claim 33, wherein the distal end of the pushing wire is held in position by the lubricious tubing and the second lumen wall.

35. The catheter of claim 29, wherein the portion of the second lumen proximal to the opening has been heat shrunk around the pushing wire.

36. The catheter of claim 29, which comprises at least one additional coextensive lumen having open proximal and distal ends.

37. The catheter of claim 36, wherein there is one additional lumen.

38. The catheter of claim 29, wherein the second lumen is capable of receiving a guidewire in a sliding fit.

39. The catheter of claim 29, wherein the second lumen comprises lubricious material.

40. The catheter of claim 39, wherein the lubricious material is in the form of tubing within the second lumen.

41. The catheter of claim 38 which comprises at least one additional coextensive lumen having open proximal and distal ends.

42. The catheter of claim 41, wherein there is one additional lumen.

43. A balloon dilatation catheter system which comprises one or more catheters of claim 29 and a guidewire.

44. The system of claim 43, wherein each catheter has a dilatation balloon of varying size.

* * * * *